US012008755B2

(12) United States Patent
Bokhari et al.

(10) Patent No.: US 12,008,755 B2
(45) Date of Patent: Jun. 11, 2024

(54) CHROMOSOMAL ENHANCEMENT AND AUTOMATIC DETECTION OF CHROMOSOMAL ABNORMALITIES USING CHROMOSOMAL IDEOGRAMS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Yahya Abdulfattah Bokhari, Riyadh (SA); Areej Abdulaziz Alhareeri, Riyadh (SA); Azizah Mohammed Alkhaldi, Riyadh (SA); Abdulrhman Fahad Aljouie, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 625 days.

(21) Appl. No.: 17/204,286

(22) Filed: Mar. 17, 2021

(65) Prior Publication Data
US 2021/0295518 A1 Sep. 23, 2021

Related U.S. Application Data

(60) Provisional application No. 62/990,713, filed on Mar. 17, 2020.

(51) Int. Cl.
G06T 7/00 (2017.01)
G06T 5/70 (2024.01)
(Continued)

(52) U.S. Cl.
CPC .............. *G06T 7/0014* (2013.01); *G06T 5/80* (2024.01); *G16B 20/20* (2019.02); *G16B 45/00* (2019.02);
(Continued)

(58) Field of Classification Search
None
See application file for complete search history.

(56) References Cited

U.S. PATENT DOCUMENTS

2014/0016843 A1* 1/2014 Zhang ................. G06V 20/698
382/129

FOREIGN PATENT DOCUMENTS

CN 110265087 A * 9/2019
CN 110265087 A 9/2019
(Continued)

OTHER PUBLICATIONS

Legrand et al., "Automated Identification of Chromosome Segments Involved in Translocations by Combining Spectral Karyotyping and Banding Analysis," in IEEE Transactions on Systems, Man, and Cybernetics—Part A: Systems and Humans, Nov. 2008, doi: 10.1109/TSMCA.2008.2003963 (Year: 2008).*
(Continued)

*Primary Examiner* — Vu Le
*Assistant Examiner* — Charles C L Penny
(74) *Attorney, Agent, or Firm* — Oblon, McClelland, Maier & Neustadt, L.L.P.

(57) ABSTRACT

A method for detecting chromosomal abnormalities comprising conversion of a chromosomal image into an ideogram which is compared to a control or standard ideogram of a chromosome; or converting an ideogram of a chromosome into a chromosomal image.

20 Claims, 22 Drawing Sheets

(51) Int. Cl.
*G06T 5/80* (2024.01)
*G16B 20/20* (2019.01)
*G16B 45/00* (2019.01)

(52) U.S. Cl.
CPC ...... *G06T 5/70* (2024.01); *G06T 2207/10056* (2013.01); *G06T 2207/20081* (2013.01); *G06T 2207/30072* (2013.01)

(56) References Cited

FOREIGN PATENT DOCUMENTS

| EP | 3432198 A2 * | 1/2019 | .......... G06K 9/0014 |
|---|---|---|---|
| WO | WO 99/22026 A1 | 5/1999 | |

OTHER PUBLICATIONS

Sharma et al., "Crowdsourcing for Chromosome Segmentation and Deep Classification," 2017 IEEE Conference on Computer Vision and Pattern Recognition Workshops (CVPRW), Honolulu, HI, USA, 2017, pp. 786-793, doi: 10.1109/CVPRW.2017.109 (Year: 2017).*

Yirui Wu, Xiao Tan, Tong Lu, and Xuyun Zhang. A New Multiple-Distribution GAN Model to Solve Complexity in End-to-End Chromosome Karyotyping. Complex. 2020 (2020). doi: 10.1155/2020/8923838 (Year: 2020).*

John Pavlopoulos, Vasiliki Kougia, and Ion Androutsopoulos. 2019. "A Survey on Biomedical Image Captioning". In Proceedings of the Second Workshop on Shortcomings in Vision and Language, pp. 26-36, Minneapolis, Minnesota. Association for Computational Linguistics (Year: 2019).*

Yu-Ping Wang, Qiang Wu, K. R. Castleman and Zixiang Xiong, "Chromosome image enhancement using multiscale differential operators," in IEEE Transactions on Medical Imaging, vol. 22, No. 5, pp. 685-693, May 2003, doi: 10.1109/TMI.2003.812255. (Year: 2003).*

Qiang Wu, Zhongmin Liu, T. Chen, Zixiang Xiong and K. R. Castleman, "Subspace-based prototyping and classification of chromosome images," in IEEE Transactions on Image Processing, vol. 14, No. 9, pp. 1277-1287, Sep. 2005, doi: 10.1109/TIP.2005.852468. (Year: 2005).*

S. Khan, A. DSouza, J. Sanches and R. Ventura, "Geometric correction of deformed chromosomes for automatic Karyotyping," 2012 Annual International Conference of the IEEE Engineering in Medicine and Biology Society, San Diego, CA, USA, 2012, pp. 4438-4441, doi: 10.1109/EMBC.2012.6346951. (Year: 2012).*

X. Zhou, Y. Lu and Z. Yan, "Image Completion for Overlapping Chromosomes," 2008 IEEE Pacific-Asia Workshop on Computational Intelligence and Industrial Application, Wuhan, China, 2008, pp. 413-417, doi: 10.1109/PACIIA.2008.271. (Year: 2008).*

W. C. Schwartzkopf, A. C. Bovik and B. L. Evans, "Maximum-likelihood techniques for joint segmentation-classification of multispectral chromosome images," in IEEE Transactions on Medical Imaging, vol. 24, No. 12, pp. 1593-1610, Dec. 2005, doi: 10.1109/TMI.2005.859207. (Year: 2005).*

W. Wu, "Dynamic Modeling of G-Banded Human Chromosomes for Cytogenetics Education." Order No. 1493744, Purdue University, United States—Indiana, 2010. (Year: 2010).*

B. Legrand,et al., "Automated Identification of Chromosome Segments Involved in Translocations by Combining Spectral Karyotyping and Banding Analysis," in IEEE Transactions on Systems, Man, and Cybernetics, vol. 38, No. 6, pp. 1374-1384, Nov. 2008, doi: 10.1109/TSMCA.2008.2003963 (Year: 2008).*

B. Levy and R. Wapner, "Prenatal diagnosis by chromosomal microarray analysis," Fertility and Sterility, vol. 109, No. 2, pp. 201-212, Feb. 2018. doi: 10.1016/j.fertnstert.2018.01.005 (Year: 2018).*

R S Remya, et al., "Computer aided method for the detection of structural abnormalities in acute lymphocytic leukemia from the g-banded karyotypes", 2018 International CET Conference on Control, Communication, and Computing (IC4), Jul. 5-7, 2018, pp. 346-351.

Denise M Duarte, et al., "Chromosomal characterization of cryopreserved mesenchymal stem cells from the human subendothelium umbilical cord vein", Regenerative Medicine, vol. 7, No. 2, Mar. 2012, 2 pages (Abstract only).

"fast.ai—Making neural nets uncool again", https://www.fast.ai/, 2021, 34 pages.

Justin Johnson, et al., "Perceptual Losses for Real-Time Style Transfer and Super-Resolution", Computer Science, Computer Vision and Patter Recognition (cs.CV); Machine Learning (cs.LG), https://arxiv.org/abs/1603.08155, arXiv:1603.08155v1, Mar. 27, 2016, 3 pages (Abstract only).

Jun-Yan Zhu, et al., "Unpaired Image-to-Image Translation using Cycle-Consistent Adversarial Networks", IEEE International Conference on Computer Vision (ICCV), arXiv:1703.10593, https://junyanz.github.io/CycleGAN/, 2017, 10 pages (Abstract only).

* cited by examiner

Cryptic deletion of chromosome 2

Converting chromosomal ideogram into chromosome

Chromosomal enhancement

CHROMOSOMAL ENHANCEMENT AND AUTOMATIC DETECTION OF CHROMOSOMAL ABNORMALITIES USING CHROMOSOMAL IDEOGRAMS

CROSS-REFERENCE TO RELATED APPLICATION

This application claims priority to U.S. Provisional Application No. 62/990,713, filed Mar. 17, 2020, which is hereby incorporated by reference for all purposes.

BACKGROUND OF THE INVENTION

Field of Invention

Cytogenetic medical instrumentation and methods using artificial intelligence.

Description of Related Art

Chromosomal analysis or karyotyping is typically performed in a cytogenetics laboratory. Karyotyping is a process in which the number and visual appearance of the chromosomes in the cell nuclei of an organism or species is determined. Existing protocols use a microscope which can visualize metaphase chromosomes (FIG. 1A), a camera to photograph the chromosomes, and software to help classify and organize chromosomes in a sample (FIG. 1B).

Conventional procedures can detect abnormalities in chromosome number, for example, a missing or additional chromosome, or large abnormalities such as deletion of a portion of a chromosome. However, certain chromosomal abnormalities, such as short, cryptic deletions to a chromosome (FIG. 2A) are difficult to detect and often require review by a cytogeneticist with years of experience. Manual efforts to identify prominent bands in a micrographic image by creating an ideogram of a chromosome can miss such cryptic deletions (FIG. 6). Thus, chromosomal abnormalities often get missed because of the complex efforts required to analyze micrographic images of chromosomes containing abnormalities.

In view of these problems, the inventors sought to apply artificial intelligence to clarify micrographic images and to rapidly and accurately determine karyotype and detect abnormalities difficult or impossible to detect by present methods.

BRIEF SUMMARY OF THE INVENTION

Aspects of the invention include a method and system that permit accurate and sensitive identification of abnormalities in micrographic images of chromosomes. The method and system convert micrographic images of chromosomes into an intermediate phase (ideograms) in which software can more easily analyze and precisely predict presence of a chromosomal abnormality.

This system solves an inconvenient bottle neck in conventional methods used in a cytogenetic laboratory, namely, analyzing the chromosomes in karyotype images to discover the abnormalities or to identify abnormalities that require human clarification. Elements of this system are depicted by FIG. 3B.

Aspects of the invention include, but are not limited to, the following.

A system for detecting chromosomal abnormalities comprising, consisting essentially of, or consisting of obtaining micrographic images of metaphase which consists usually of 23 pairs of chromosomes. from a subject, converting the micrographic images into its 23 pairs of ideograms depicting a banding pattern on the one or more chromosomes, comparing the ideograms to control ideograms of corresponding chromosomes, and identifying differences between the ideograms and the control ideograms (or the lack of differences), wherein said difference indicates an abnormality or putative abnormality in the chromosomes; and, optionally, treating the subject for a disease, disorder, or condition associated with the chromosomal abnormality when a difference is identified. Finally, reporting the abnormalities based on ISCN guidelines. This system can be employed to compare chromosomal images produced from ideograms with actual chromosomal images or to compare ideograms made from chromosomal images with control ideograms.

A related aspect of the invention is a computer-implemented method for detecting chromosomal abnormalities comprising, consisting essentially of, or consisting of obtaining micrographic images of one, two, three, four, five, six, seven, eight, nine, ten or more chromosomes from a subject, converting the micrographic images into one or more ideograms depicting a banding pattern on the one or more chromosomes, comparing the ideograms to control ideograms of corresponding chromosomes, and identifying differences between the ideograms and the control ideograms (or the lack of differences), wherein said difference indicates an abnormality or putative abnormality in the chromosomes; and, optionally, treating the subject for a disease, disorder, or condition associated with the chromosomal abnormality when a difference is identified. Such diseases or disorders include all diseases which fall under constitutional abnormalities such as balance and unbalanced chromosome translocations. Also included are diseases characterized by neoplasm abnormalities including, but not limited to, chronic myeloid leukemia (CML) and multiple myeloma.

In some embodiments of this method, obtaining micrographic images comprises obtaining two or more micrographic images of a chromosome.

In some embodiments, of this method, converting the micrographic images into one or more ideograms is performed manually using a subset of chromosome images thereby creating a paired set of chromosomes and ideograms which are used to train a model. Multiple chromosomal images or ideograms may be used to train the model.

In other embodiments of this method, the converting the micrographic images into one or more ideograms is performed using imaging processing by passing an image of a chromosome through a function that outputs its ideogram.

In another embodiment of this method, the converting the micrographic images into one or more ideograms is performed using cycle-GAN software to produce ideograms with random banding, which are bent and curved to random shapes that mimic natural bends and curves in the imaged chromosomes. Ideograms may be bent or curved using image-to-image translation or pix2pix translation; see Phillip Isola, et al., *Image-to-Image Translation with Conditional Adversarial* Networks, arXiv:1611.07004 (cs) [Submitted on 21 Nov. 2016 (v1), last revised 26 Nov. 2018 (this version, v3)] which is incorporated by reference.

Ideograms may be curved prior to being fed into Cycle-GAN to build a richer and more robust system. Moreover, in order for Cycle-GAN to efficiently function, the shapes of the two domains must be similar.

Cycle-GAN software is publically or commercially available, for example, as described by Zhu, J. et al., *Unpaired*

*Image-to-Image Translation using Cycle-Consistent Adversarial Networks*, in IEEE International Conference on Computer Vision (ICCV), 2017 (incorporated by reference).

Real chromosomal images are input into a Domain A in Cycle-GAN and a chromosomal ideogram into a Domain B. Cycle-GAN outputs both a conversion of the real image or images into an ideogram and vice-versa. This builds and trains the model. A trained model will recognize a new instance of a chromosomal image which is passed into the system and converted into a chromosomal ideogram. In the same manner, an image of an ideogram which is passed into the system can be converted to a chromosomal image. The general objective is to generate an ideogram when the system is fed with chromosome images and to generate chromosome images when it is fed with ideograms.

In some embodiments, the identifying any difference between the ideograms and the control ideograms comprises manual visual inspection of the ideograms and control ideograms or evaluation of the ideograms and control ideograms using artificial intelligence.

In some embodiments of this method, it further comprises classifying the chromosome as normal, abnormal, or potentially abnormal, for example, based on comparison to a control ideogram.

Other embodiments of this method may further comprise providing computer-generated text or a report, such as a cytogenetics report, describing one or more chromosomal abnormalities.

In some embodiments, this method further comprises enhancing the micrographic images of the one or more chromosomes, prior to converting the images of ideograms.

In other embodiments, the method comprises converting the micrographic image into an ideogram and then converting the ideogram to a standard ideogram.

In some embodiments, converting the micrographic image comprises converting it to an ideogram and enhancing the micrographic image using the ideogram without adding or deleting information.

In some embodiments of this method, the control ideogram(s) are of normal human chromosomes.

In other embodiments, the control ideogram(s) are of abnormal human chromosomes.

In some embodiments, the control ideogram(s) are those described by the International System for Human Cytogenetic Nomenclature (ISCN-2005). However, ideograms from other sources may be used as well.

In certain embodiments of this method, it further comprises producing a karyotype of chromosomes in the sample.

In other embodiments of this method it further comprises identifying employs the ideogram to identify an exact break point of a chromosome.

In some embodiments of this method the said identifying employs the ideogram to identify a chromosomal deletion, a chromosomal duplication, a chromosomal inversion, and/or a chromosomal translocation.

Other embodiments include a system, apparatus or equipment for performing the methods disclosed herein which may include equipment and supplies for staining chromosomes, microscopes for viewing chromosomes, cameras or scanners for obtaining images of stained chromosomes, computer equipment and software for transmitting or processing images, software for comparing images or ideographs to control images or ideographs, software for identifying and classifying particular chromosomal abnormalities, and outputs for displaying images or for producing cytogenetics reports.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

DETAILED DESCRIPTION OF THE INVENTION

Figure 1A:
FIG. 1A. A metaphase spread from a cell.
Figure 1B:
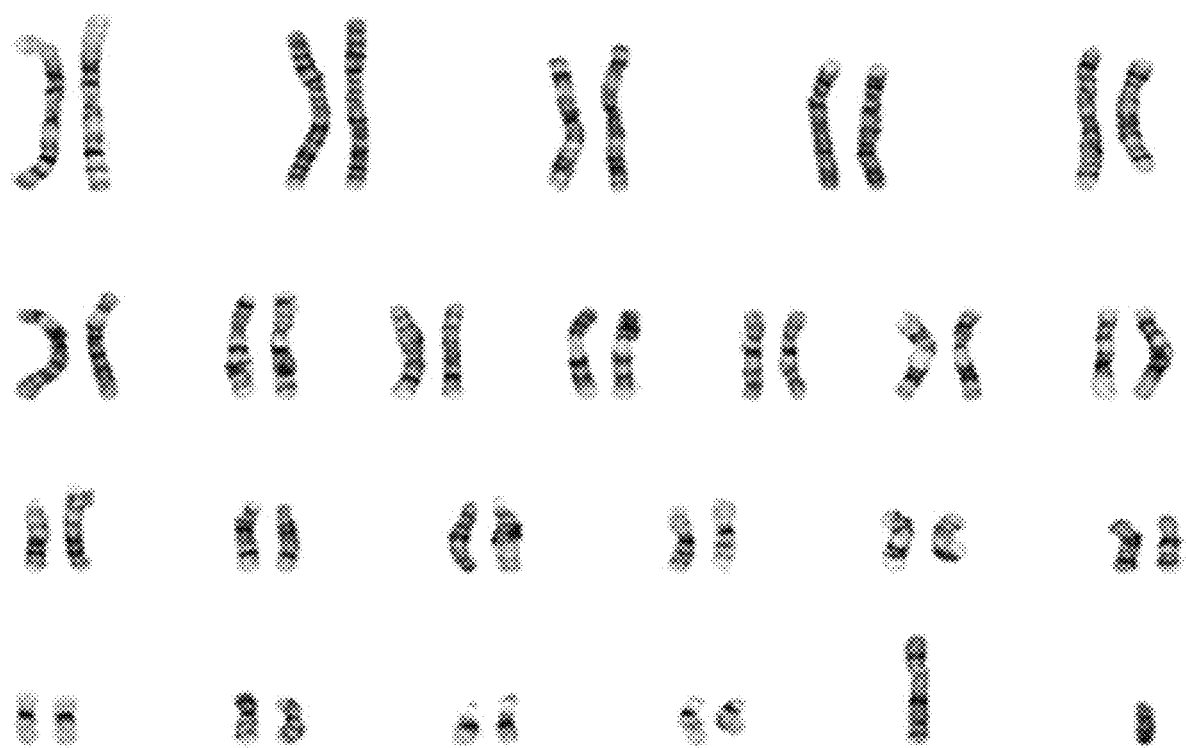
FIG. 1B. A karyogram generated by chromosomal karyotyping.

The present invention provides methods for producing an accurate karyotype from images of chromosomes, such as metaphase chromosomes which have optionally been stained to exhibit discrete bands. The disclosed method converts images of chromosomes into ideograms of chromosomes which can then be compared to control ideograms to identify locations where chromosomal discontinuities, defects, rearrangements and/or aberrations occur. A preferred method for converting chromosomal images into ideograms or ideograms to chromosomal images uses Cycle-GAN.

Conventional karyotyping is laborious and often requires highly specialized experts to the limitations of conventional methods. The method and system disclosed herein pertain to analysis of chromosomal banding on metaphase chromosomes and uses artificial intelligence (generative adversarial networks) to enhance and convert bands in a photomicrograph of metaphase chromosomes to ideograms for sensitive and rapid detection of variations, usually abnormalities, in chromosomal banding.

During the second stage of cell division, between prophase and anaphase, the chromosomes become attached to the spindle fibers. Karyotyping is done at metaphase because metaphase is the only stage in cell cycle when the chromosomes are unduplicated and line up along the equatorial plate of the spindle. The chromosomes are easier to see when they are elongated and uncondensed.

Chromosome banding is used mainly to identify both normal and rearranged chromosomes, to define chromosome breakpoints, and to describe the specific location of DNA sequences on chromosomes. A nomenclature has been developed to standardize the identification of chromosomes and the naming of chromosome bands. The system currently in use is *An International System for Human Cytogenetic Nomenclature*, referred to as "ISCN 1995." The report includes a chromosome band nomenclature, as well as standard ideograms, which are "diagrammatic representations of a karyotype, which may be based on measurements of the chromosomes" (ISCN 1995). The ISCN-1995 report, its nomenclature and ideograms are incorporated by reference.

A chromosome abnormality, chromosomal anomaly, chromosomal aberration, chromosomal mutation, or chromosomal disorder, is a missing, extra, or irregular portion of chromosomal DNA. These can occur in the form of numerical abnormalities, where there is an atypical number of chromosomes, or as structural abnormalities, where one or more individual chromosomes are altered. Chromosome mutation was formerly used in a strict sense to mean a change in a chromosomal segment, involving more than one gene. Chromosome anomalies usually occur when there is an error in cell division following meiosis or mitosis. Chromosome abnormalities may be detected or confirmed by comparing an individual's karyotype, or full set of chromosomes, to a typical karyotype for the species via genetic testing Abnormalities may include deletions, duplications (associated with Charcot-Marie-Tooth disease type 1A), inversions, translocations, reciprocal translocation, Robersonian translocations (chromosomes 13, 14, 15, 21 and 22), rings, or isochromosome.

Other chromosomal abnormalities are associated with cancer cells. Karyotypic abnormalities have been described in more than 10,000 human neoplasms analyzed by means of chromosome banding. These aberrations are of three different kinds: primary abnormalities, which are essential in establishing the tumor; secondary abnormalities, which develop only after the neoplasm is established but which nevertheless may be important in tumor progression; and cytogenetic noise, which is the background level of non-consequential aberrations. These latter changes are, in contrast to the primary and secondary aberrations, randomly distributed throughout the genome. The primary abnormalities, of which more than 100 have been identified, are strictly correlated with particular neoplastic disorders and even with histopathological subgroups within a given tumor type. One aspect of the invention involves identifying abnormal chromosomal arrangements in a cancer patient or patient at risk of cancer. Cancers include hematologic cancers as well as solid tumors such as prostate cancer and non-small cell lung cancer. The system disclosed herein detects chromosomal abnormalities which can be associated with particular diseases, disorders, or conditions. Cycle-GAN is employed to generate an ideogram from a chromosomal image, or an image from a chromosomal ideogram, thus facilitating characterization of chromosomal abnormalities.

A full account of a karyotype may therefore include the number, type, shape and banding of the chromosomes, as well as other cytogenetic information.

Karyotyping is the process by which photographs of chromosomes are taken in order to determine the chromosome complement of an individual, including the number of chromosomes and any abnormalities. The term is also used for the complete set of chromosomes in a species or in an individual organism and for a test that detects this complement or measures the number.

Karyotypes describe the chromosome count of an organism and what these chromosomes look like under a light microscope. Attention is paid to their length, the position of the centromeres, banding pattern, any differences between the sex chromosomes, and any other physical characteristics. The preparation and study of karyotypes is part of cytogenetics.

The study of karyotypes is made possible by staining. Usually, a suitable dye, such as Giemsa is applied after cells have been arrested during cell division by a solution of colchicine usually in metaphase or prometaphase when most condensed. In order for the Giemsa stain to adhere correctly, all chromosomal proteins must be digested and removed. For humans, white blood cells are used most frequently because they are easily induced to divide and grow in tissue culture. Sometimes observations may be made on non-dividing (interphase) cells.

The method as disclosed herein may be used to identify differences between or among different chromosome or between a chromosomal image and an ideogram. Preferably, these differences are reflected in banding patterns. Chromosome banding refers to alternating light and dark regions along the length of a chromosome, produced after staining with a dye. Dyes include fluorochromes or fluorescent dyes such as those described by WO99/22026 (incorporated by reference). These include, but are not limited to, a counterstain fluorochrome DAPI(4'-6-diamidino-2-phenylindole) which attaches to all chromosomes present in the metaphase; and three other non-counterstain fluorochromes FITC (fluorescein isothiocyanate), Cy3 and Cy5 which attach and stain only specific parts of the respective chromosomes. Each fluorochrome is preferably excited to fluoresce upon illumination by a specific band or range of wavelengths of light. Fluorescent images of chromosomal banding patterns may be illuminated and processed by those skilled in the art or by the methods described by WO99/22026 (incorporated by reference). Other dyes, illumination sources, or imaging methods that produce images of chromosome banding patterns may be used in the methods disclosed herein.

A band is defined as the part of a chromosome that is clearly distinguishable from its adjacent segments by appearing darker or lighter with the use of one or more banding techniques. For example, deletion, duplication or translocation of parts of a chromosome can result in differences in banding patterns compared to a chromosome not having the deletion, duplication or translocation.

Other differences in karyotypes which may be determined by, or in combination with the methods disclosed herein include differences in absolute sizes of chromosomes. Chromosomes can vary in absolute size by as much as twenty-fold between genera of the same family. Size can be calculated on the length, width, height or area of the chromosomal image. Differences in the position of centromeres. These differences probably came about through translocations. Positional differences may be neighboring transpositions or transposition separating by intervening centromeres. Differences in basic number of chromosomes. Differences in number and position of satellites. Satellites are small bodies attached to a chromosome by a thin thread. Differences in degree and distribution of heterochromatic regions. Heterochromatin stains darker than euchromatin. Heterochromatin is packed tighter. Heterochromatin consists mainly of genetically inactive and repetitive DNA sequences as well as containing a larger amount of Adenine-Thymine pairs. Euchromatin is usually under active transcription and stains much lighter as it has less affinity for the Giemsa stain. Euchromatin regions contain larger amounts of Guanine-Cytosine pairs. The staining technique using Giemsa staining is called G banding and therefore produces the typical "G-Bands".

As a cell divides, during metaphase, the chromosomes all line up in the center of the cell. Microtubules attach to the chromosomes and pull them apart, so half the DNA ends up in each daughter cell. Before the DNA gets pulled apart, the chromosomes are free to recombine. For example, paternal and maternal copies of chromosome 5 can recombine producing a mix of chromosomal sequences from both parents. During recombination, the chromosomes must break and reattach. "Chromosomal breakpoints" refers to these places where they break. Occasionally something goes wrong and the reattachment happens in the wrong place producing an aberrant chromosome which is often associated with some type of abnormality. Usually the term "chromosomal breakpoints" is used in the context of such an abnormality.

Generative Adversarial Networks, or GANs for short, are an approach to generative modeling using deep learning methods, such as convolutional neural networks. Generative modeling is an unsupervised learning task in machine learning that involves automatically discovering and learning the regularities or patterns in input data in such a way that the model can be used to generate or output new examples that plausibly could have been drawn from the original dataset. GANs train a generative model by framing the problem as a supervised learning problem with two sub-models: the generator model that is trained to generate new examples, and the discriminator model that tries to classify examples as either real (from the domain) or fake (generated). The two models are trained together in a zero-sum game, adversarial, until the discriminator model is fooled about half the time, meaning the generator model is generating plausible examples. In some embodiments, other generative adversarial networks besides Cycle-GAN, such as variant Cycle-GAN architectures, may be used as part of the systems and methods disclosed herein.

The Cycle Generative Adversarial Network, or Cycle-GAN, is an approach to training a deep convolutional neural network for image-to-image translation tasks. Unlike other GAN models for image translation, the CycleGAN does not require a dataset of paired images. For example, if one is interested in translating photographs of oranges to apples, one does not require a training dataset of oranges that have been manually converted to apples. This allows the development of a translation model on problems where training datasets may not exist, such as translating paintings to photographs or translating abnormalities in a micrograph of a chromosome to an ideogram of the abnormal chromosome, which can then be easily compared to an ideogram of a normal chromosome.

Figure 2:
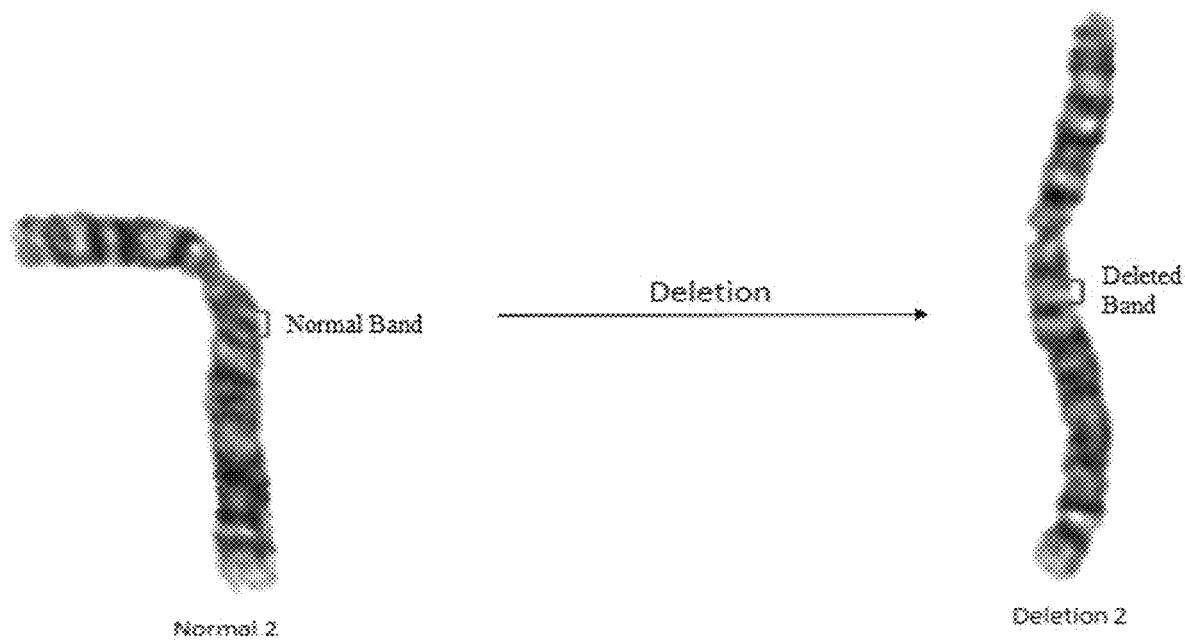
FIG. 2. Detection of a micro-deletion is difficult by both human and machine.

The system disclosed herein overcomes many of the problems associated with conventional cytogenetic analysis and karyotyping. These include detection of chromosomal abnormalities in the karyotype and an ability to provide the exact break point of the abnormality present. Technologists with less experience are prone to make errors, especially in detecting cryptic or micro-deletion chromosomal abnormalities. Existing methods are not sensitive for detecting those deletions or identifying their locations (FIG. 2A). The method and system of the present disclosure can identify and flag the presence of a chromosomal abnormality and thereby provide a second opinion in identifying these abnormalities.

The system disclosed herein also provides chromosomal enhancement without adding or removing any information. Not all cultured cytogenetic specimens provide metaphasic images of good quality, thus, not all images captured are of high quality resulting in great variation in the quality of produced images. Furthermore, image enhancement is hampered by the limitations of traditional image processing software.

Another advantage of the system disclosed herein is its capacity to generate a complex or normal chromosome starting from a random ideogram (a barcode like imag). As a hallmark of cancer, genomic instability produces complex structural rearrangements in patients with cancer. Although those complex chromosomes consist of pieces of normal chromosomes, predicting the origin of the different pieces comprising those complex chromosomes is a difficult task even for cytogenetics experts. Oftentimes, cytogenetics scientists hypothesize the origin of the complex chromosome and generate an ideogram by cutting and gluing ISCN ideograms to generate the bands (lines) of the complex chromosome. Once the hypothesized complex ideogram is built manually, they compare its bands to the complex chromosome for confirmation, Interestingly, cytogenetic testing for patients with cancer is a routine work and comprises about 50-70% of the workload in the majority of cytogenetics labs.

Writing the karyotype is considered another challenging and time consuming task in cytogenetic testing. Cytogeneticists follow the ISCN guidelines to write down the karyotype for a given patient. Challenging parts in this process are knowing the type of abnormality present and pointing out the breakpoint (the place where a break on a chromosome takes place in order for a structural rearrangement, to occur) in order to write the karyotype correctly. Taking presence of various possible chromosomal abnormalities as well as the presence of different bands and sub-bands in each chromosome into consideration, a model or software that can aid in this process would be of great benefit in reducing the time needed in nomenclature writing. The disclosed system provides a superior way to write a karyotype.

The method and system disclosed herein provide the following advantages.

Figure 3A:
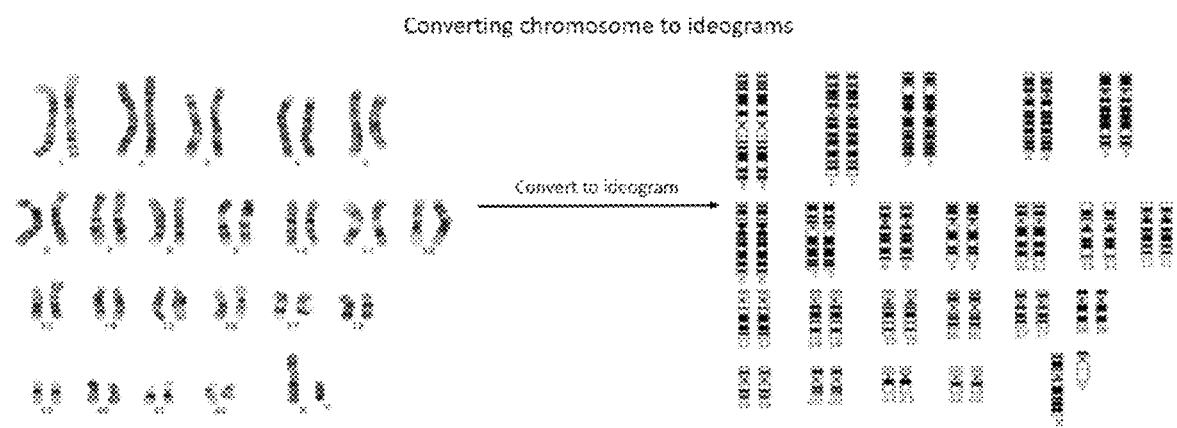
FIG. 3A. Conversion of image of chromosomal karyotype (left) into ideograms (right).
Figure 3B:
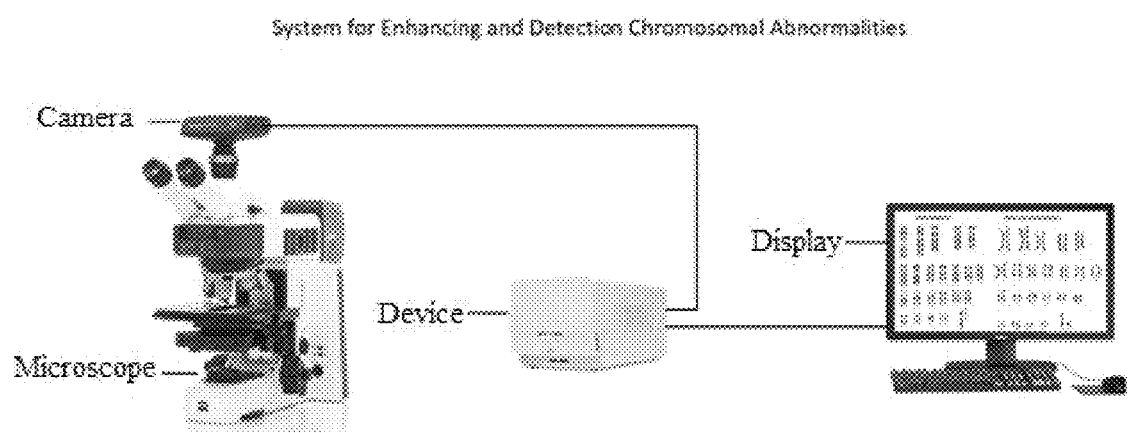
FIG. 3B. Elements of a system for producing images of chromosomes and converting them into ideograms. Metaphase chromosomes are stained and observed under a microscope. Image data is transmitted to a device that converts the images into ideograms, which are displayed adjacent to the original images.
Figure 4:
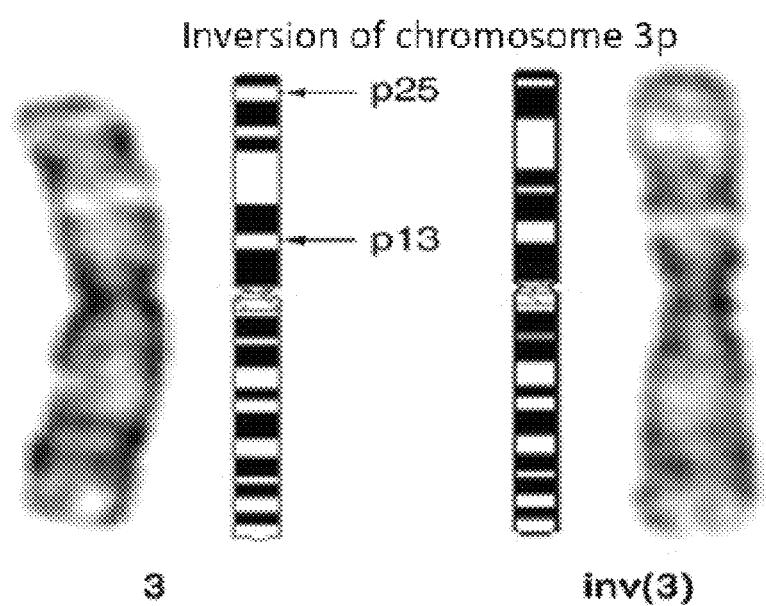
FIG. 4. Chromosomal inversions are easily seen by comparison of ideograms in contrast to chromosomal images.

The method and system can be used to convert a karyotype image into an ideogram image (FIG. 3). The step of converting the karyogram into an intermediate phase, namely, ideogram karyogram, eases the analytical process for both the technologist and the machine-aided system. For example, as illustrated in FIG. 4, it is difficult to see that there is an inversion (a segment of a chromosome that is reversed end to end) in the original chromosome 3 compare the photomicrographs on both sides of the corresponding ideograms. However, it is this abnormal inversion becomes readily apparent when comparing the two ideograms of chromosome 3.

Figure 5:
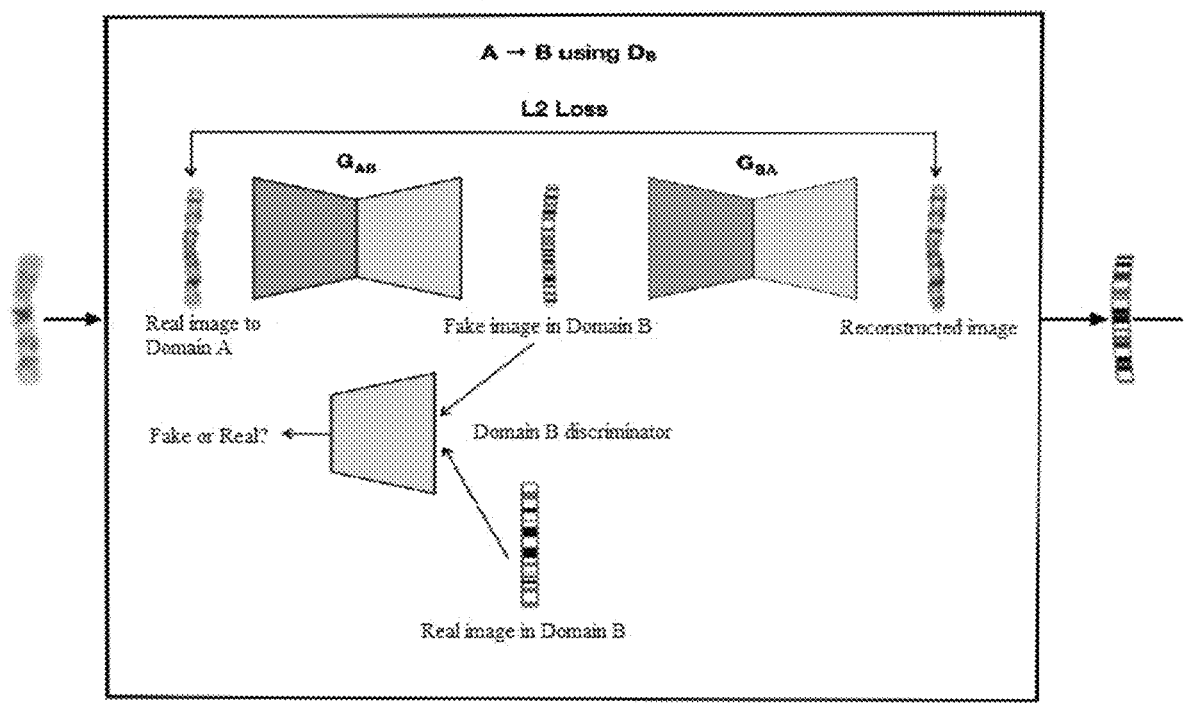
FIG. 5. Cycle-GAN (Cycle Generative Adversarial Network) is employed to convert an image of a chromosome into an ideogram.

To convert chromosome karyograms (photomicrographic images) into ideograms the inventors studied and applied generative adversarial networks GANs specifically, Cycle-GAN (FIG. 5). One option for analyzing micrographic images is by feature extraction and/or segmentation. The feature extraction described in Remya et al. can be used for feature extraction in the invention, see "Computer Aided Method for the Detection of Structural Abnormalities in Acute Lymphocytic Leukemia from the G-banded Karyotypes", 2018 International CET Conference on Control, Communication, and Computing (IC4), Jul. 5-7, 2018, pp. 346-351 incorporated herein by reference in its entirety.

The ideograms used in the system can be generated in three ways.

Figure 6:
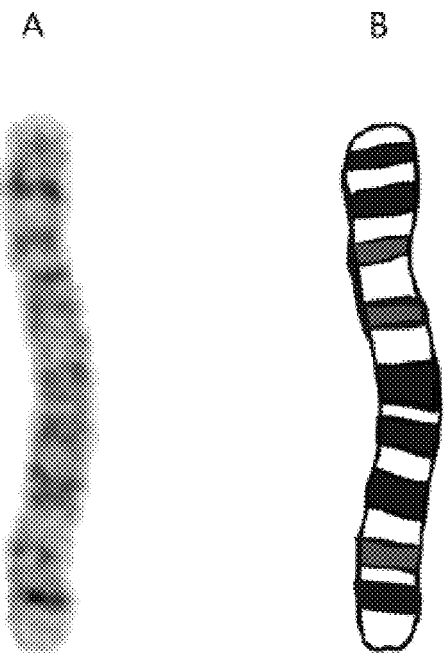
FIG. 6 compares an image of chromosome 5 (A, left) with a manually labelled chromosome 5 B, right).

In the first way, a subset of chromosome images is selected to be labeled by a cytogeneticist. These labels are basically manually created ideograms by coloring each band of a given chromosome to match its corresponding band in the ISCN template ideogram (FIG. 6). This creates a paired set of chromosomes and ideograms, which is then used to train a model. For example, an electronic device such as a tablet or laptop computer may be used to manually annotated or draw an ideogram over a real chromosomal image. The annotated images are then used to train a cycler-GAN model. The trained model is then used to predict a real chromosomal image once given an ideogram as an input.

This model outputs ideograms when provided with a given set of chromosomes. Alternatively, the model outputs chromosomal images when provided with a given set of ideograms.

The second way is to use an image processing technique in which a chromosome image is passed through a function that outputs its ideogram. In comparison to the previous approach, this method does not require manual labeling. Such a function may be developed in-house by those skilled in the art, for example, by using sine functions. Similar curving can be produced using polynomial functions, cosine functions and Fourier transformations.

The third possible way is to use CycleGAN with random chromosomal ideograms that have been generated by software. The software generates random ideograms that have random bands, Those ideograms are then bent and curved to random shapes that mimic those natural bends and curves in original chromosomes.

In order for cycle-GAN to work the two set of images have to have some similarities in shape. For example, cycle-GAN has been used to process images of horses and zebras, or oranges and apples, which have similar shapes, To train cycle-GAN, ideograms similar in shape with the chromosomes are used. Typically, ideograms are straight and the real chromosomes are curved. Accordingly a function, such as a sine function, is used to curve the ideograms before using them in CycleGAN.

Figure 7:
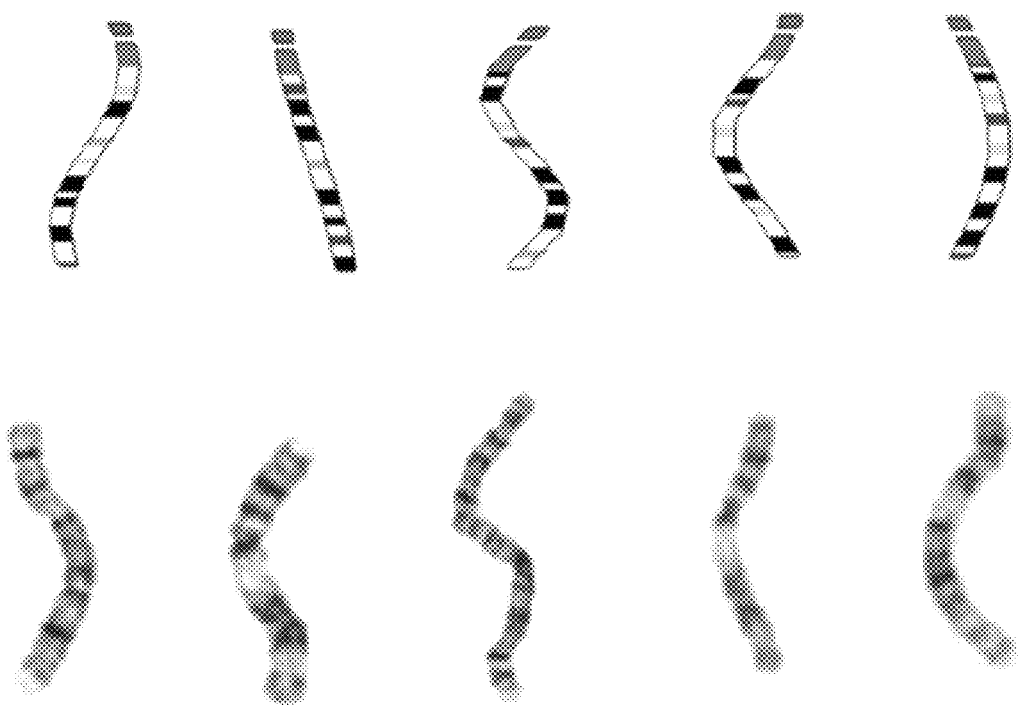
FIG. 7. Randomly generated ideograms (top 5 diagrams) are generated which are then mathematically modified to mimic the real curves (shapes) of images of real chromosomes (5 images at bottom). Note that the bands are not paired. This shows ideogram shapes that can be used to optimize CycleGANs.

Bending and curving is accomplished using polynomial, sine and cosine functions. FIG. 7: The top of the FIG. 7 contains randomly generated ideograms that are mathematically modified to mimic the real curve (shape) of the real chromosome at the bottom—note that the bands are not paired. This is shows how ideograms shapes are generated. Shapes can be used to improve and/or enhance Cycle GANs.

Figure 8:
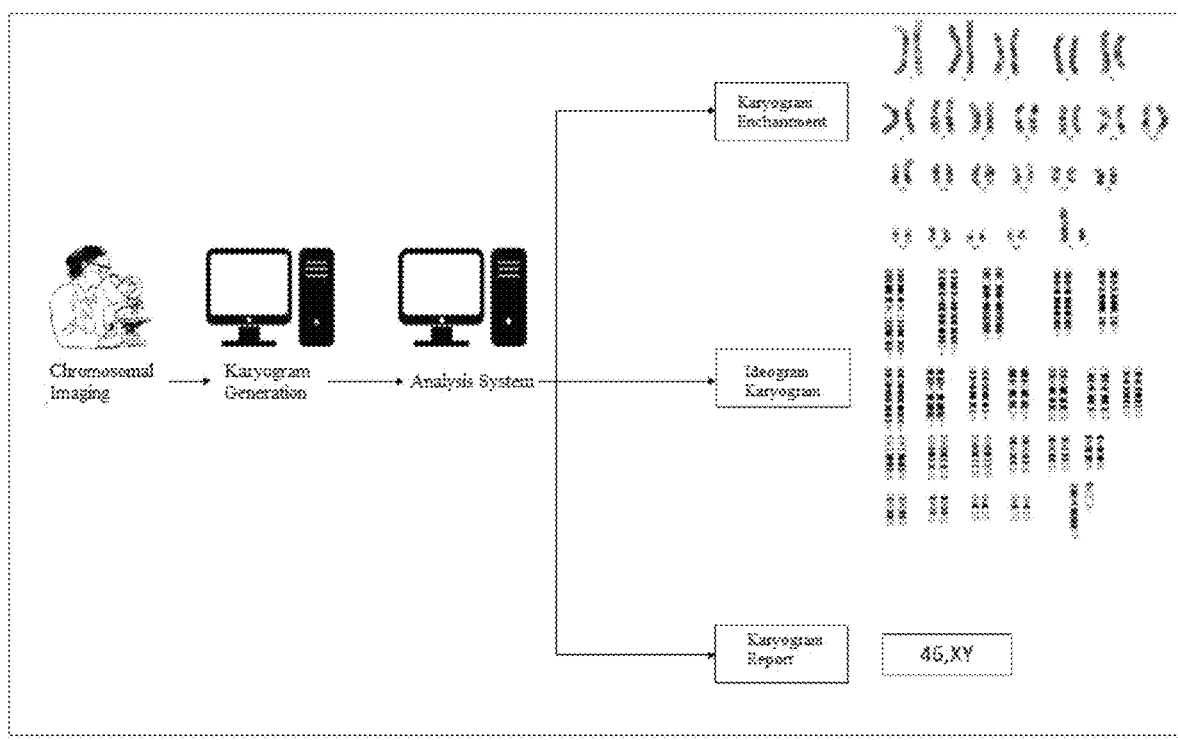
FIG. 8 depicts a system that can enhance chromosomal karyograms, convert chromosomal karyograms into ideograms, and generate reports describing the karyotype.

The disclosed system solves the main bottleneck of the cytogenetic laboratory, which is analyzing the chromosomes in the karyotype images to identify abnormalities or at least query some abnormalities that require further human investigation. FIG. 8 shows the whole system in one embodiment. The system enhances chromosomal karyograms by converting chromosomal karyograms into ideograms and generating reports that have the karyotype. This system may be applied to images of a single chromosome or to images of two or more chromosomes.

Figure 9:
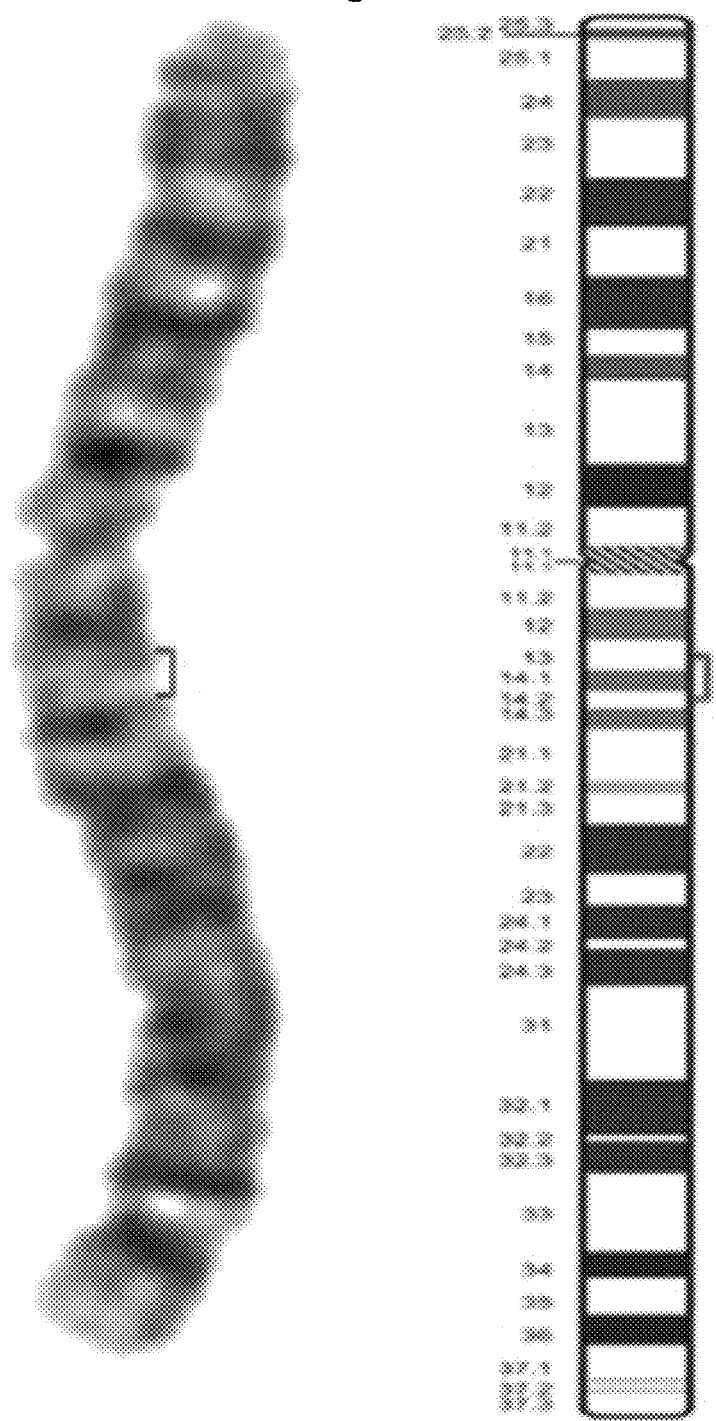
FIG. 9 illustrates the difficulty in identifying a chromosome (left) that has a deletion and to identify the break point of the deletion with respect to ICSN (International System for Chromosome Nomenclature) without use of an ISCN ideogram. Ideograms are incorporated by reference to the Atlas of Genetics and Cytogenetics in Oncology and Haematology available at hypertext transfer protocol://atlasgeneticsoncology.org/ISCN09/ISCN09.html (last accessed Mar. 11, 2021).
Figure 10:
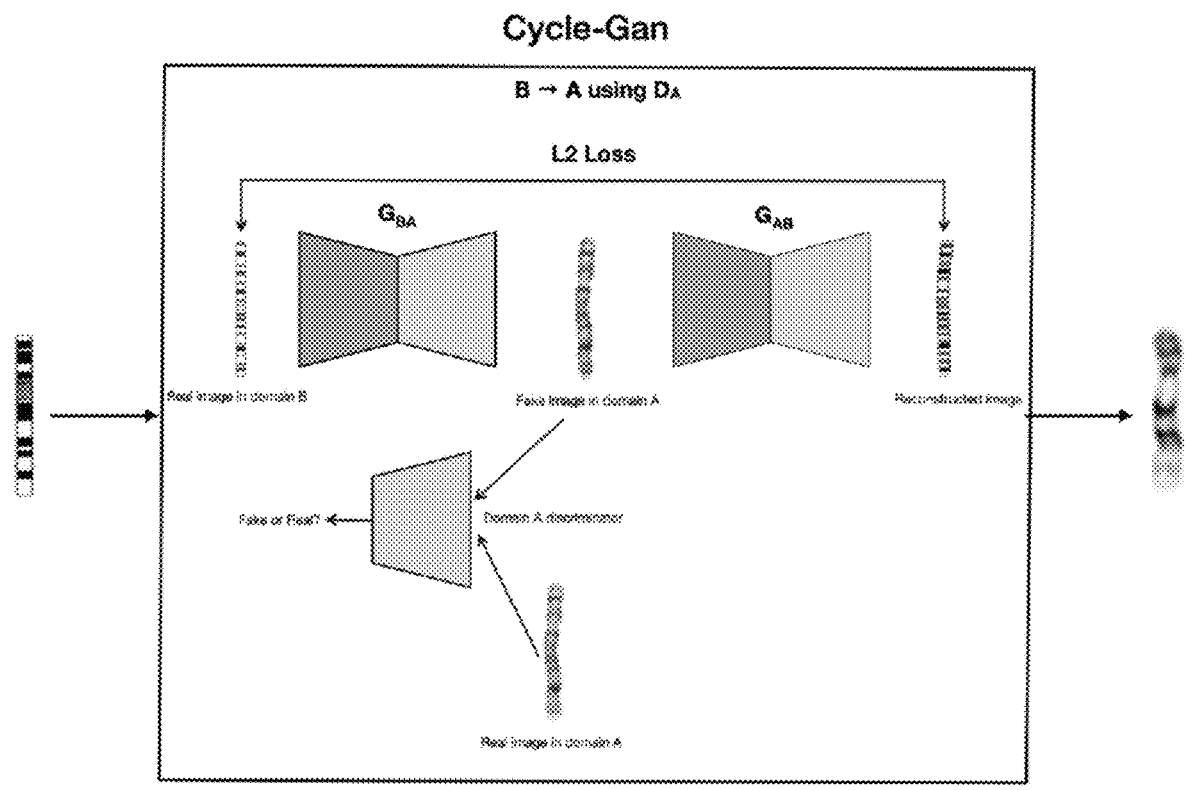
FIG. 10 depicts use of Cycle-GAN. After training, the neural networks (cycle-GAN), the system will be able to receive chromosome ideograms as input and output the real chromosomes.
Figure 11:
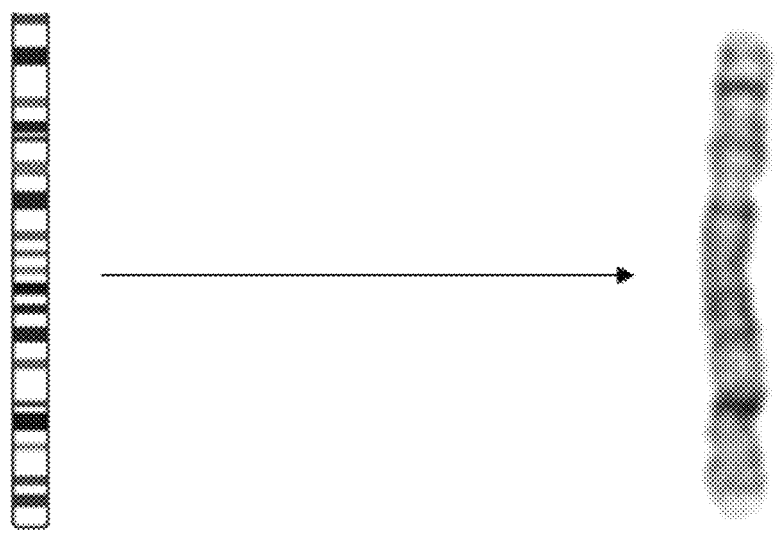
FIG. 11 illustrates converting a chromosomal ideogram into a chromosome image which permits confirmation of the bands with respect to a standard ISCN ideogram.

The system permits one to identify the abnormality break point of a chromosome without looking at the reference ideogram from ISCN (FIG. 9), As apparent from FIG. 9, it is difficult to identify that chromosome has a deletion and it is more difficult to find the break point of the deletion with respect to ISCN without looking at the ISCN ideograms Another feature of the disclosed system is the ability to convert an ideogram into an image of a real chromosome. Oftentimes due to malignancy, chromosomes acquire complex aberrations that can result in malformed complex chromosomes. In those chromosomes, it is hard to identify which band comes from which chromosome. Typically, scientists cut ideograms manually and glue them together in order to compare the chromosomal lines (bands) to confirm theoretical abnormalities. Here, the inventors provide system that uses Cycle-GAN (FIG. 10) with normal or random ideograms to output normal or complex chromosomes as shown by FIG. 11. Following that, a cytogeneticist can compare the software generated chromosome to the original abnormal one for confirmation. After training the neural networks via cycle-GAN, the system is able to receive chromosome ideograms as input and output images of the real chromosomes. As shown by FIG. 11, the system converts a chromosome ideogram into an image of a real chromosome to confirm the bands with respect to standard ISCN ideogram.

One of the issues that prevents auto-analysis of chromosomes is the poor quality of captured images. Poor image quality negatively affects the analytical process by increasing the analysis time even for an expert cytogeneticist.

Figure 12:
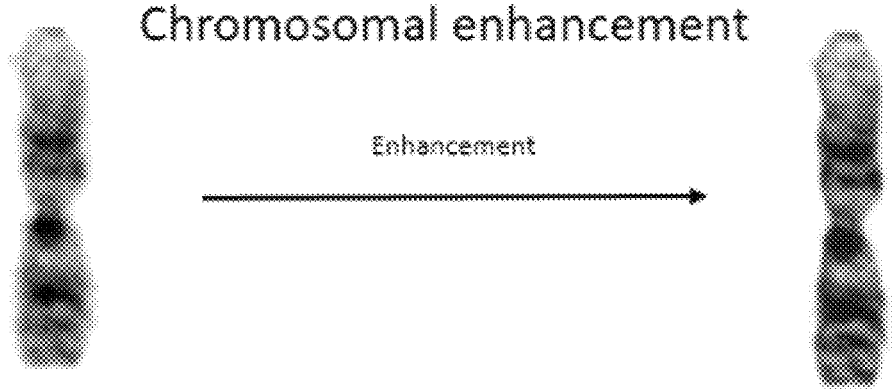
FIG. 12 depicts chromosomal enhancement which makes a tradeoff between sharpness and the presence of telomeres.

In the system disclosed herein an enhancement of the chromosomes using the reconstructed chromosome images using the above mentioned methods is produced. This enhancement is accomplished without adding or removing any chromosomal regions. FIG. 12 shows that enhancing the chromosome is critical and has a tradeoff between sharpness and the presence of telomeres The system utilizes the popular U-net and VGG (FIG. 13) architectures as a first step to generate a chromosome with better image quality, the system then passes the generated image into a network that compares it to its ideogram generated from Cycle-GAN. This accelerates the time for analysis and reduces the chances of missing abnormalities.

Figure 13:
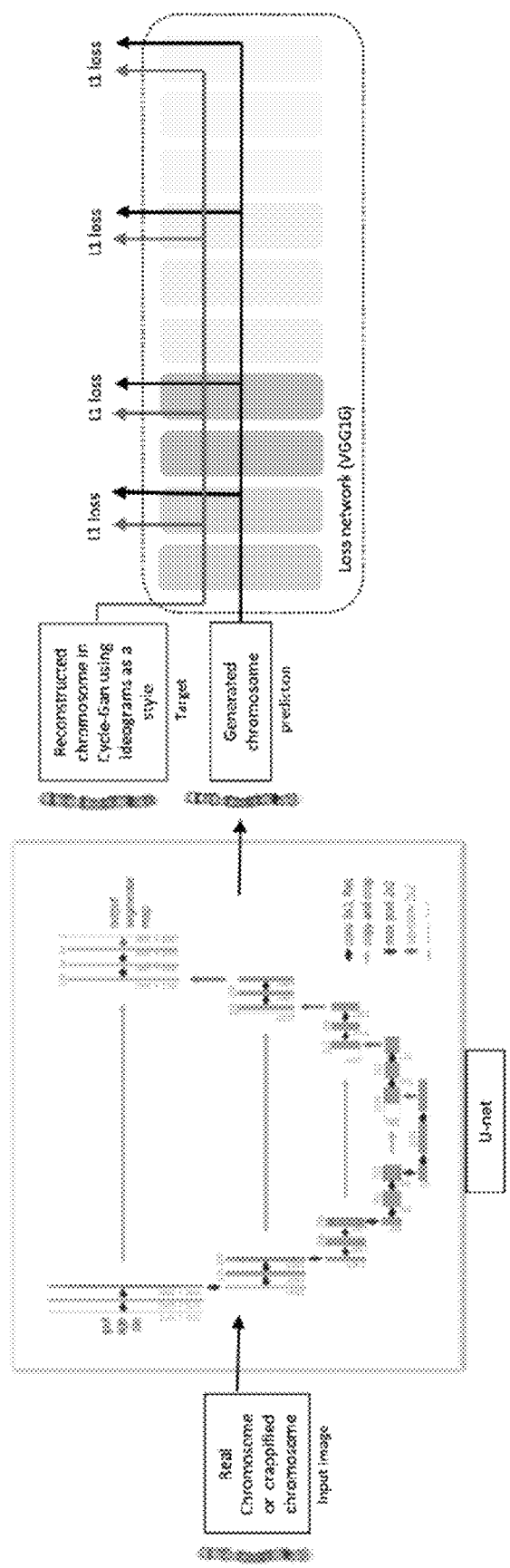
FIG. 13 describes using a U-net structure as training model transforming a real or distorted image to generate an enhanced image of a fixed chromosome. A pre-trained VGG network was used as a loss network. The 11 loss compared the generated image and a reconstructed image of Cycle-GAN described above.

FIG. 13. Using U-net structure as a training model to transform the real or distorted image to generate and enhance high quality chromosomes. Furthermore, a pretrained VGG network as a loss network was used. The 11 loss compared the generated image and reconstructed image of Cycle-GAN described above.

Figure 14:
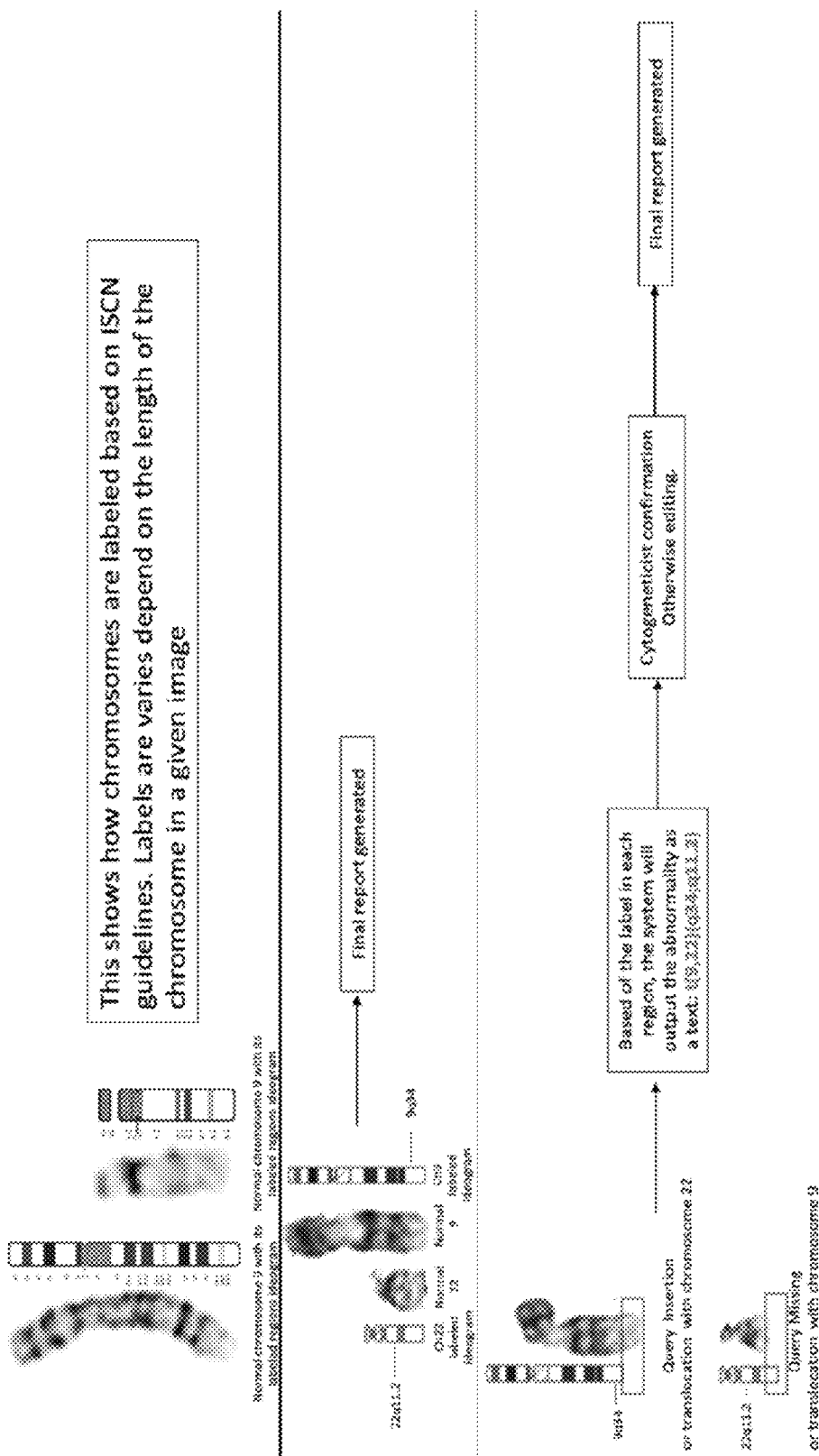
FIG. 14 describes how the system labels chromosomes and generates text reports based on ISCN guidelines.

Another feature of the system disclosed herein is that with the help of cytogenetic technologists, the system generates text that describes the abnormalities according to ISCN guidelines. Based on ISCN, each chromosome is divided into labeled known regions. Once an abnormality is detected, the system can generate a report according to those regions. In other words, if there is a newly generated chromosome, based on the labeled regions the system will report which band belongs to which chromosome according to ISCN guidelines. If there is no abnormality in the chromosomes, the system will report a normal male or a normal female karyotype according to ISCN (FIG. 14).

Figure 15:
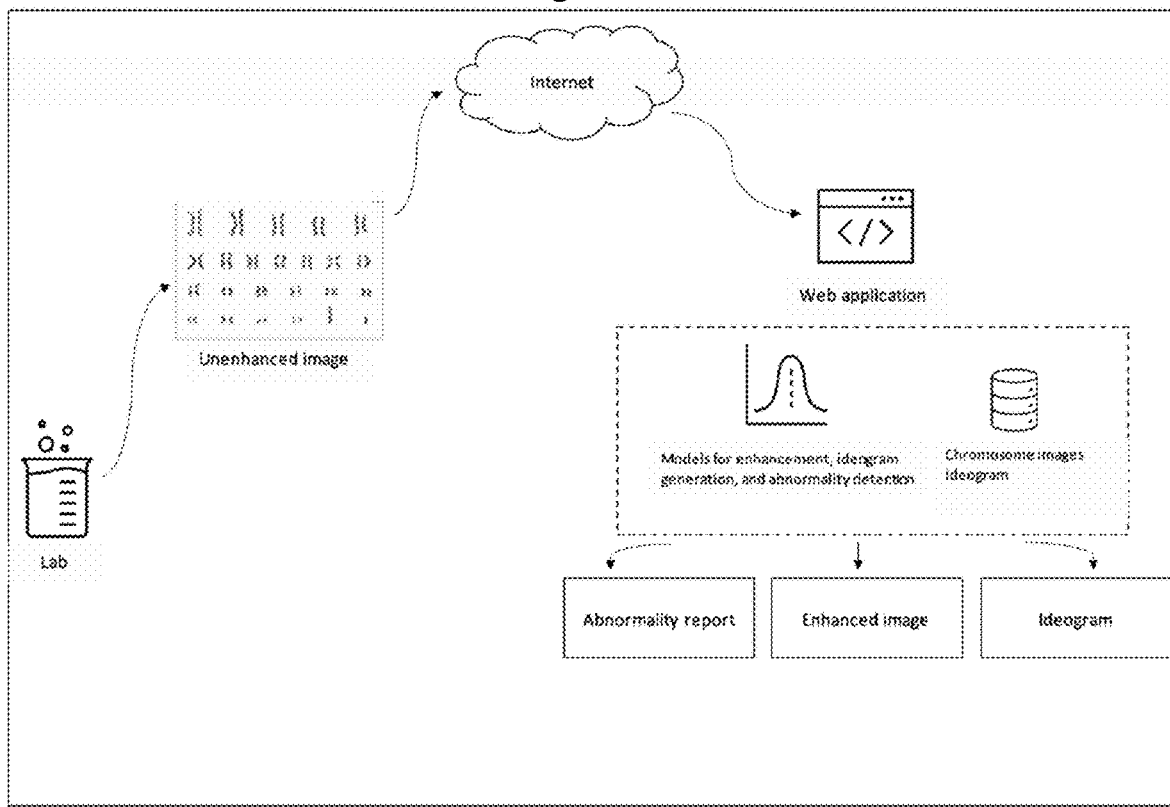
FIG. 15 illustrates how the system disclosed herein can use an internet connection of web application which sends an unenhanced karyotype image via a connection and the application reports the abnormality and displays an enhanced image and its corresponding ideogram.

The system may be deployed on a web server where lab technologists submit images so that the system can produce a high quality image along with an ideogram and an abnormality detection report. FIG. 15 provides a diagram that describes the disclosed system using internet connection and web application where a lab sends an unenhanced image of karyotype via a connection and the app reports the abnormality, the enhanced image and its corresponding ideogram.

Figure 16:
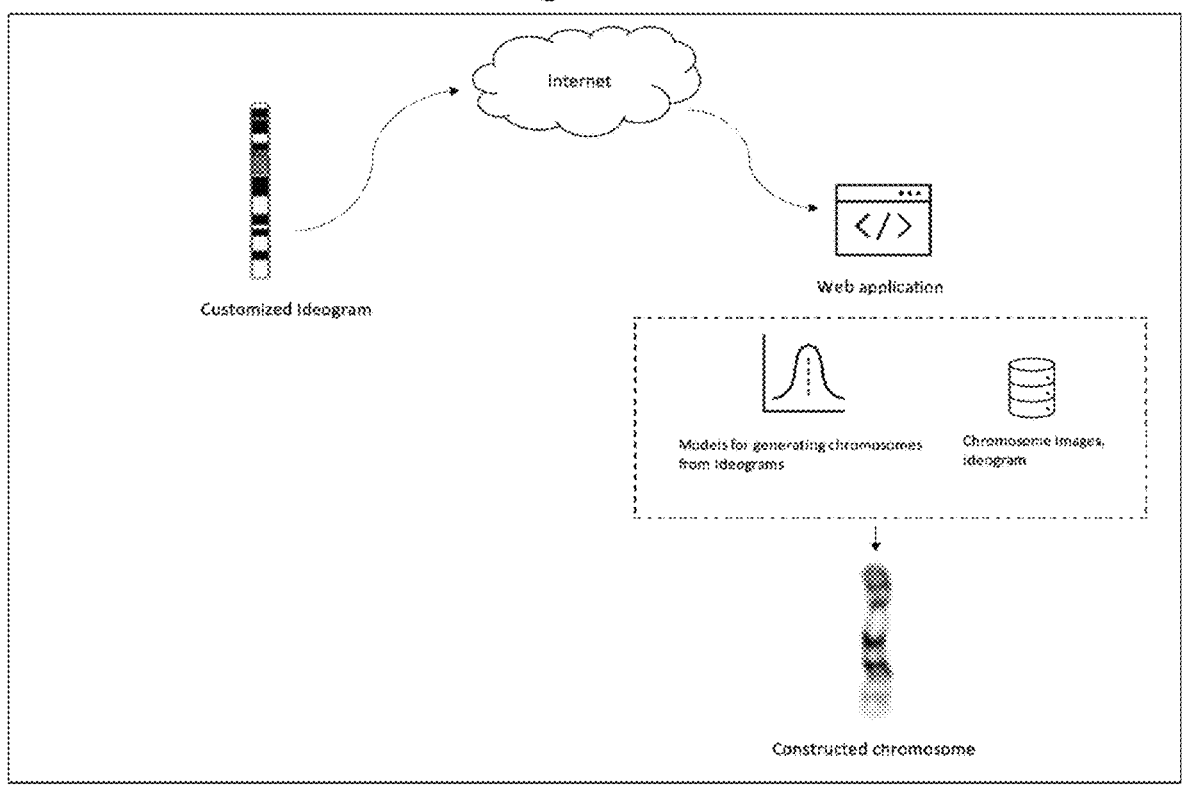
FIG. 16 shows how the system can be deployed on a web-server to convert customized ideogram to a constructed chromosomal image.
Figure 17:
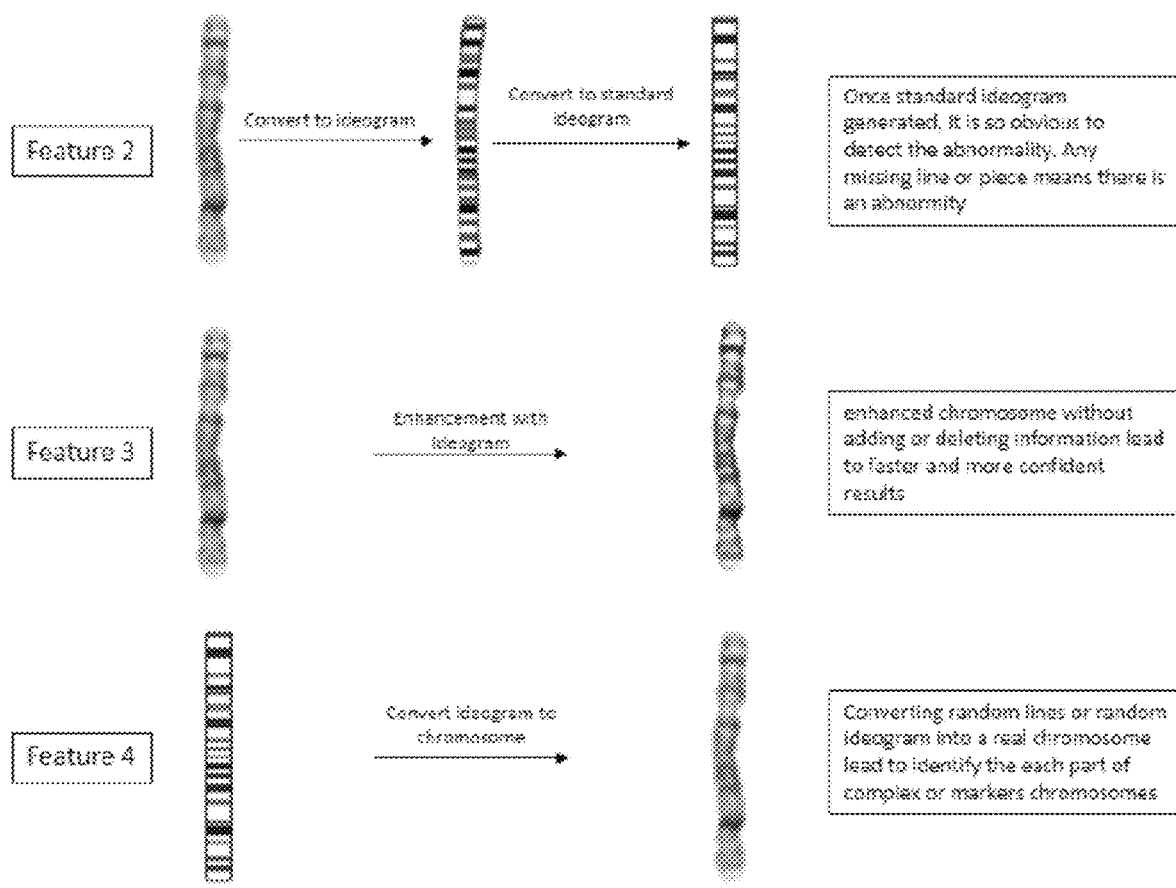
FIG. 17 shows some features of the invention including conversion of chromosomal image to ideogram, enhancement of chromosomal image, and conversion of random ideogram into a chromosomal image.

The web server contains a data set of images and ideograms that are used to construct a model that generates an enhanced image when given an unenhanced one. With many end users utilizing the model and submitting new images, this model can be expanded or modified periodically as the database grows. In addition, the web server accepts an ideogram as an input and generates its corresponding chromosome as an output (FIG. 16). Illustrations of some of the features of the disclosed system are illustrated in FIG. 17.

The disclosed system has a number of unique features that distinguish it from conventional systems such as the *Leica Biosystems* CytoVision system.

The disclosed system converts chromosomes to an intermediate phase, namely into an ideogram which the computer can analyze and predict the abnormality. Chromosomes are converted into ideograms using cycle-GAN, a known software.

Instead of solving this problem directly, the disclosed system breaks it down into a simpler problem that can be solved using artificial intelligence while retaining all information needed in the original image. This provides for maximum enhancement of the chromosomal images without adding or subtracting information from the original image.

The ideograms produced by the disclosed system (and thus the corresponding chromosomal images) can be auto-analyzed using artificial intelligence which has not been applied in conventional systems due to the complexity of analyzing chromosomal photomicrographic images.

Conveniently, the system can also generate text that describes the abnormality according to ISCN guidelines.

As apparent from the above disclosure, the invention will lower the expense of conducting cytogenetic analysis by minimizing the number of persons needed as well as speed up the time taken for manual analysis. Cytogenetic analysis is very labor intensive and usually exhausts employees and decreases their productivity. Image enhancement provided as disclosed above will make the analytical process less labor intensive. Moreover, the analysis of multiple, redundant bands in a chromosomal image, which can produce false negative results, can be avoided by auto-analysis of the chromosomes permitting manual verification of only abnormalities highlighted by the disclosed system. The system can accept new ideograms built by cytogeneticists and convert them into chromosomal images to help confirm which chromosomes make up a given derivative chromosome. Lastly, the disclosed system helps with the complex process of writing a cytogenetic report since its software can generate nomenclature corresponding to a discovered abnormality.

Figure 22:
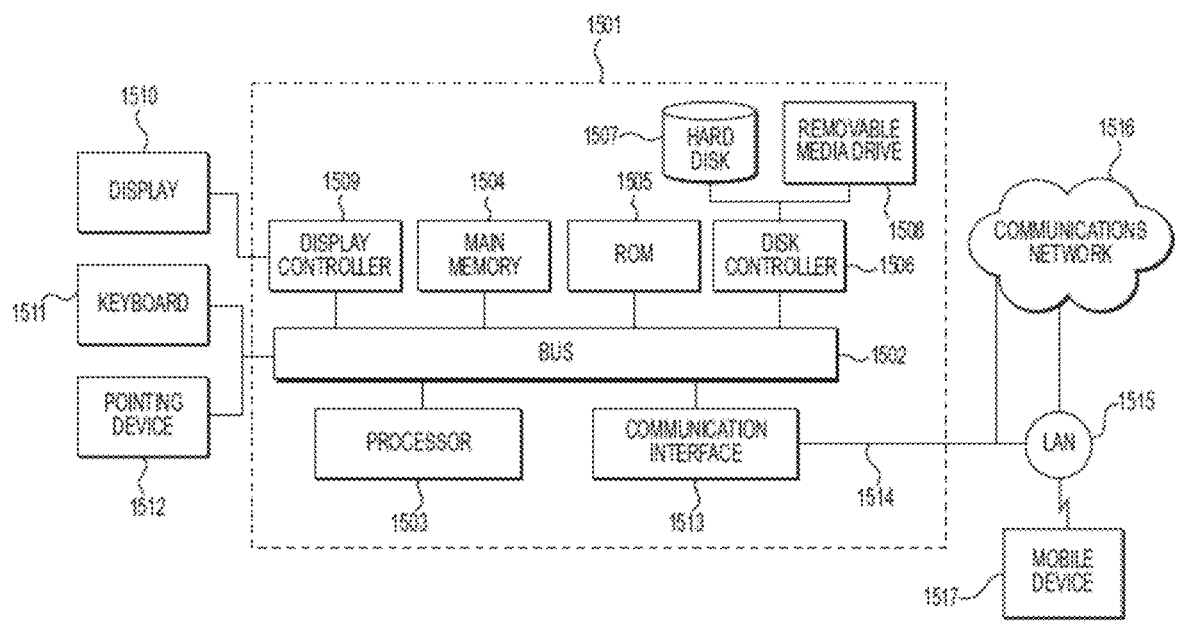
FIG. 22 describes a block diagram of a computing device according to one embodiment.

FIG. 22 illustrates a block diagram of a computing device according to one embodiment. The computer-based and software based elements of the invention, such as image enhancement, conversion of a photomicrographic image into an ideogram, the conversion of an ideogram into an image, or the use of artificial intelligence of identify chromosomal abnormalities and produce a report may be implemented on the computing devices as disclosed herein.

Each of the functions of the described embodiments may be implemented by one or more processing circuits. A processing circuit includes a programmed processor (for example, processor 1503 in FIG. 22), as a processor includes circuitry. A processing circuit also includes devices such as an application-specific integrated circuit (ASIC) and circuit components that are arranged to perform the recited functions.

The various features discussed above may be implemented by a computer system (or programmable logic). FIG. 22 illustrates such a computer system 1501. In one embodiment, the computer system 1501 is a particular, special-purpose machine when the processor 1503 is programmed to perform the functions described in the above embodiments.

The computer system 1501 includes a disk controller 1506 coupled to the bus 1502 to control one or more storage devices for storing information and instructions, such as a magnetic hard disk 1507, and a removable media drive 1508 (e.g., floppy disk drive, read only compact disc drive, read/write compact disc drive, compact disc jukebox, tape drive, and removable magneto-optical drive). The storage devices may be added to the computer system 1501 using an appropriate device interface (e.g., small computer system interface (SCSI), integrated device electronics (IDE), enhanced-IDE (E-IDE), direct memory access (DMA), or ultra-DMA).

The computer system 1501 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1501 may also include a display controller 1509 coupled to the bus 1502 to control a display 1510, for displaying information to a computer user. The computer system includes input devices, such as a keyboard 1511 and a pointing device 1512, for interacting with a computer user and providing information to the processor 1503. The pointing device 1512, for example, may be a mouse, a trackball, a finger for a touch screen sensor, or a pointing stick for communicating direction information and command selections to the processor 1503 and for controlling cursor movement on the display 1510.

The processor 1503 executes one or more sequences of one or more instructions contained in a memory, such as the main memory 1504. Such instructions may be read into the main memory 1504 from another computer readable medium, such as a hard disk 1507 or a removable media drive 1508. One or more processors in a multi-processing arrangement may also be employed to execute the sequences of instructions contained in main memory 1504. In alternative embodiments, hard-wired circuitry may be used in place of or in combination with software instructions. Thus, embodiments are not limited to any specific combination of hardware circuitry and software.

As stated above, the computer system 1501 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1501, for driving a device or devices for implementing the features of the present disclosure, and for enabling the computer system 1501 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term 'computer readable medium' as used herein refers to any non-transitory medium that participates in providing instructions to the processor 1503 for execution. A computer readable medium may take many forms, including but not limited to, non-volatile media or volatile media. Non-volatile media includes, for example, optical, magnetic disks, and magneto-optical disks, such as the hard disk 1507 or the removable media drive 1508. Volatile media includes dynamic memory, such as the main memory 1504. Transmission media, on the contrary, includes coaxial cables, copper wire and fiber optics, including the wires that make up the bus 1502. Transmission media also may also take the form of acoustic or light waves, such as those generated during radio wave and infrared data communications.

Various forms of computer readable media may be involved in carrying out one or more sequences of one or more instructions to processor 1503 for execution. For example, the instructions may initially be carried on a magnetic disk of a remote computer. The remote computer can load the instructions for implementing all or a portion of the present disclosure remotely into a dynamic memory and send the instructions over a telephone line or by Wi-Fi using a modem. A modem local to the computer system 1501 may receive the data on the telephone line and place the data on the bus 1502. The bus 1502 carries the data to the main memory 1504, from which the processor 1503 retrieves and executes the instructions. The instructions received by the main memory 1504 may optionally be stored on storage device 1507 or 1508 either before or after execution by processor 1503.

The computer system 1501 also includes a communication interface 1513 coupled to the bus 1502. The communication interface 1513 provides a two-way data communication coupling to a network link 1514 that is connected to, for example, a local area network (LAN) 1515, or to another communications network 1516 such as the Internet. For example, the communication interface 1513 may be a network interface card to attach to any packet switched LAN. As another example, the communication interface 1513 may be an integrated services digital network (ISDN) card. Wireless links may also be implemented. In any such implementation, the communication interface 1513 sends and receives electrical, electromagnetic or optical signals that carry digital data streams representing various types of information.

The network link 1514 typically provides data communication through one or more networks to other data devices. For example, the network link 1514 may provide a connection to another computer through a local network 1515 (e.g., a LAN) or through equipment operated by a service provider, which provides communication services through a communications network 1516. The local network 1514 and the communications network 1516 use, for example, electrical, electromagnetic, or optical signals that carry digital data streams, and the associated physical layer (e.g., CAT 5 cable, coaxial cable, optical fiber, etc.). The signals through the various networks and the signals on the network link 1514 and through the communication interface 1513, which carry the digital data to and from the computer system 1501 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1501 can transmit and receive data, including program code, through the network(s) 1515 and 1516, the network link 1514 and the communication interface 1513. Moreover, the network link 1514 may provide a connection through a LAN 1515 to a mobile device 1517 such as a personal digital assistant (PDA) laptop computer, or cellular telephone.

EXAMPLES

Figure 18:
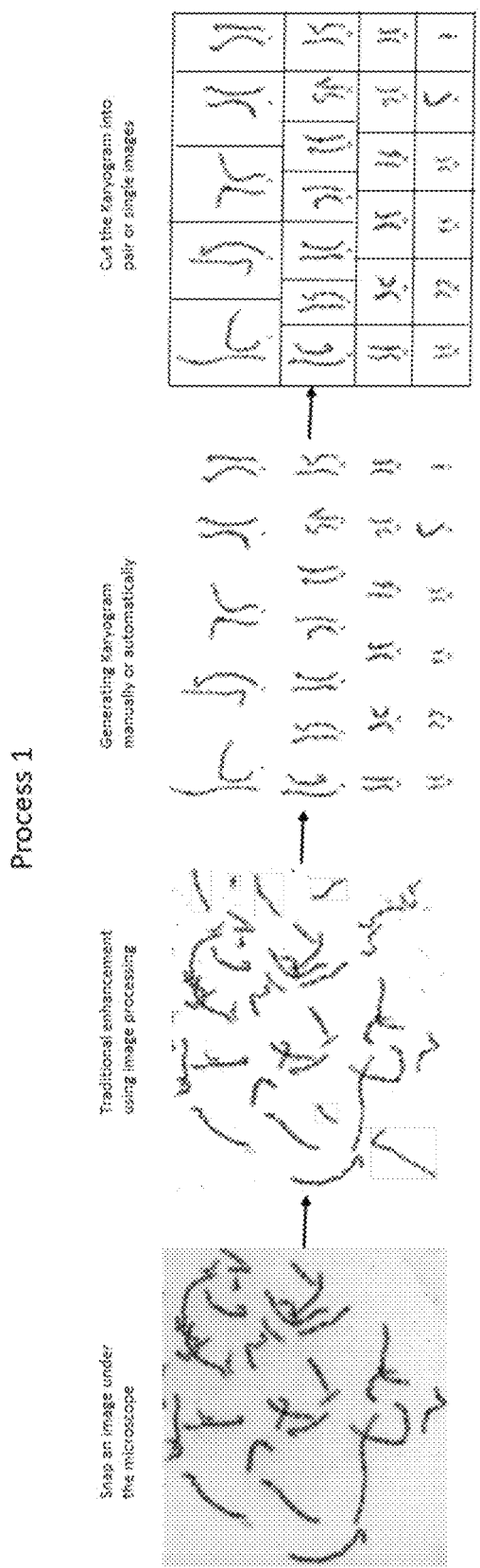
FIG. 18 describes Process 1 which is a conventional karyotyping process.
Figure 19:
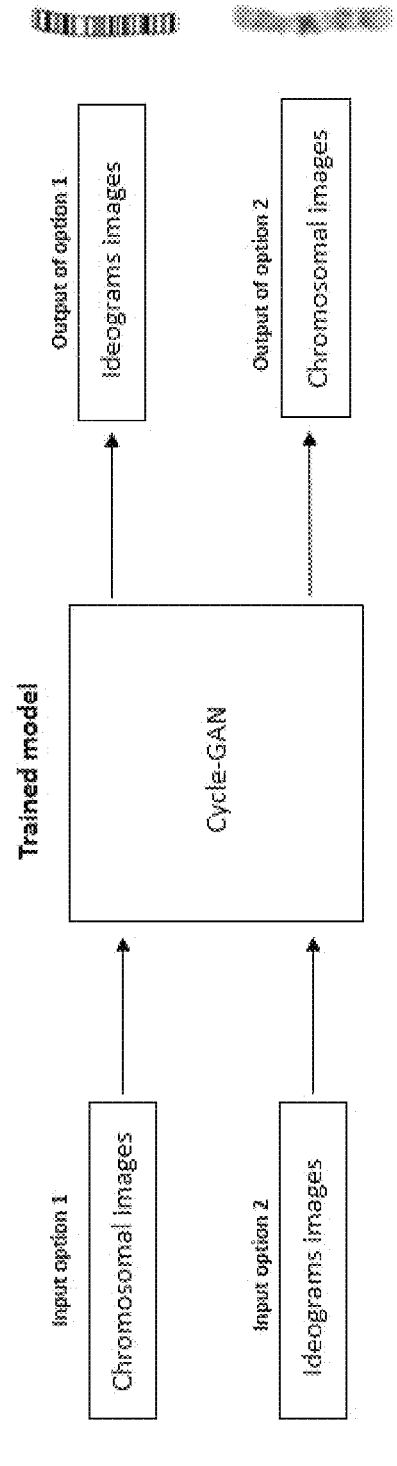
FIG. 19 describes Process 2 as disclosed herein which employs a trained Cycle-GAN model to convert chromosomal images to chromosomal ideograms, or vice-versa.
Figure 20:
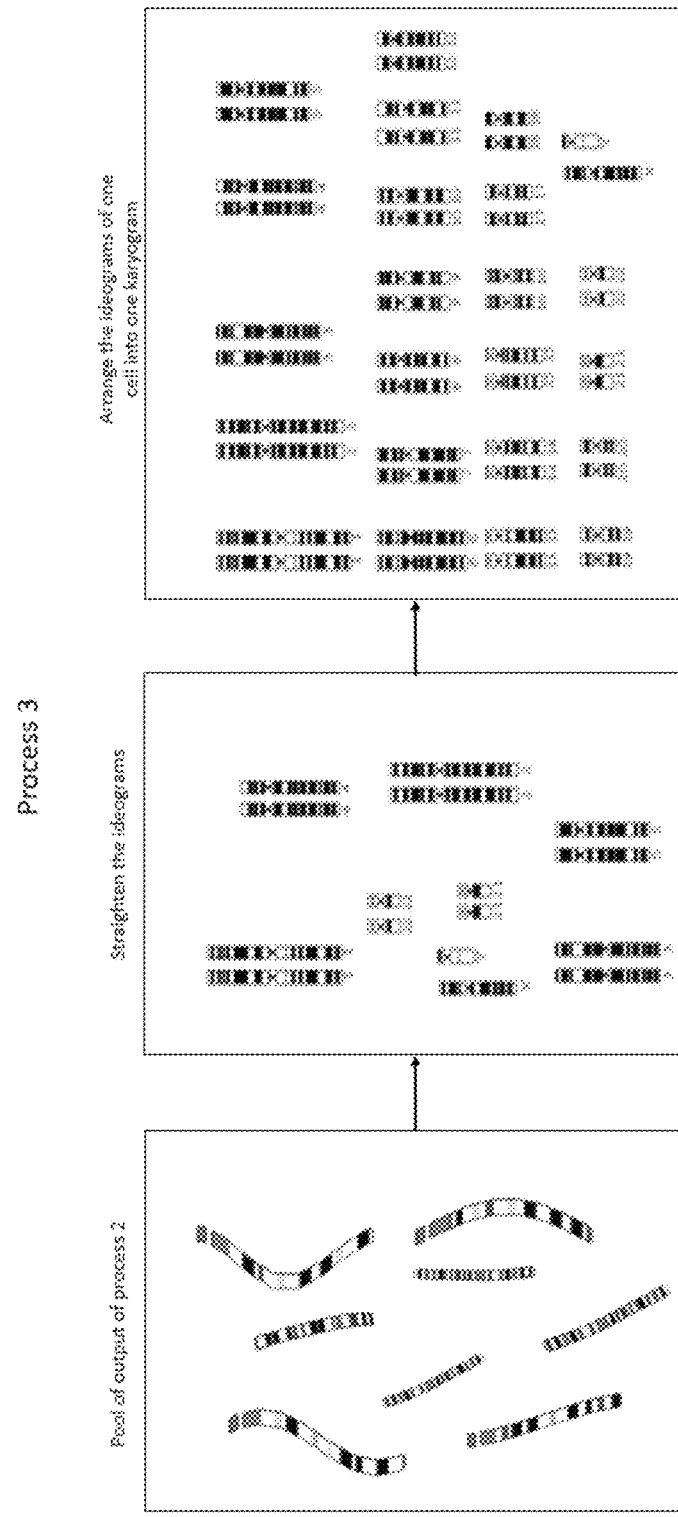
FIG. 20 describes a Process 3 as disclosed herein which uses mathematical functions to straighten images of chromosomes to facilitate their processing by Cycle-GAN.

The following graphic examples of certain embodiments of the system or methods disclosed herein are described by FIGS. 18 (Process 1), 19 (Process 2) and 20 (Process 3).

In Process 1, an image of stained chromosomes is produced (first panel), which is further clarified using conventional enhancement, such as decreasing background and increasing contrast (panel 2). Panel 3 shows the subsequent generation of a karyogram, which in panel 4 are separated into pairs of single chromosomal images. Process 1 describes a conventional process of producing a karyogram.

Process 2 describes inputting chromosomal images into a trained Cycle-GAN model, which outputs ideograms; or when given an ideogram, outputs chromosomal images. This process which is disclosed herein facilitates the identification of chromosomal abnormalities that are undetectable or difficult to accurately detect by conventional methods. The output of process 2, option 2, is used as a single chromosome.

Process 3 discloses output of a pool of ideograms derived from Process 2 which are then straightened using mathematical functions as disclosed herein, and arranged as a karyogram of ideograms. FIGS. 5 and 10 further describe this cycle-GAN-based process.

Figure 21:
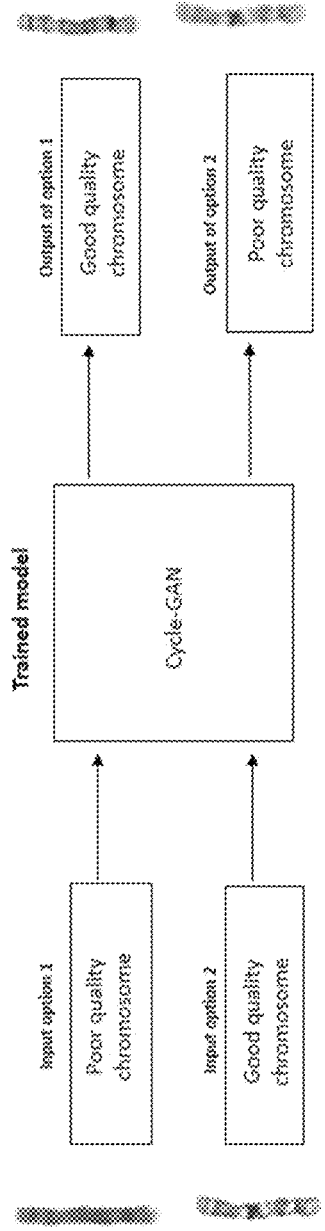
FIG. 21 describes a method for enhancing a chromosomal image.

As shown by FIG. 21, a chromosomal image may be enhanced. An enhancement module comprises a system that builds a convolutional based network which converts bad quality images into higher quality images. This model is trained to differentiate between bad and good quality images and use the features extracted from good quality images to enhance images of poorer quality.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A computer-implemented method for detecting chromosomal abnormalities cryptic deletions or putative cryptic deletions comprising:
    obtaining an image of a banding pattern of a chromosome comprising a cryptic deletion or putative cryptic deletion,
    converting the image into an ideogram depicting said banding pattern,
    comparing the ideogram to an ideogram of an image of a paired control chromosome not comprising the cryptic deletion or putative cryptic deletion, and
    identifying a difference in a banding pattern between the ideogram of the chromosome and the ideogram of the paired control chromosome,
    wherein said difference indicates a cryptic deletion or putative cryptic deletion in the imaged chromosome.

2. The method of claim 1,
    wherein the obtaining an image of a banding pattern of a chromosome comprises obtaining an image of a chromosome containing a cryptic deletion and an image of a paired control chromosome not containing the cryptic deletion,
    wherein the converting the image into an ideogram depicting said banding pattern comprises converting images of the chromosome and its paired control chromosome into ideograms, and
    wherein the identifying the difference in a banding pattern comprises identifying a difference between the ideogram of the chromosome containing the cryptic deletion and the ideogram of the second paired chromosome not containing the cryptic deletion,
    wherein the comparing of the ideogram to an ideogram of the paired control chromosome not comprising the cryptic deletion comprises comparing the banding pattern of the ideogram of the chromosome containing the cryptic deletion to the banding pattern of the ideogram of its paired chromosome not containing the cryptic deletion, thereby identifying the cryptic deletion.

3. The method of claim 1, wherein the converting an image of the chromosome comprising the cryptic deletion into an ideogram is performed manually using a subset of chromosome images thereby creating a paired set of chromosomes and ideograms which are used to train a model.

4. The method of claim 1, wherein the converting an image of the chromosome comprising the cryptic deletion into an ideogram comprises passing an image of the chromosome through a function that outputs an ideogram corresponding to the chromosomal image.

5. The method of claim 1, wherein the converting an image of a chromosome comprising the cryptic deletion into an ideogram comprises using CycleGAN with random, software-generated chromosomal ideograms, which have random bands, and then bending or curving the random shapes to mimic natural bends and curves in the chromosome image using polynomial, sine and cosine functions.

6. The method of claim 1, wherein the converting an image of the chromosome comprising the cryptic deletion into an ideogram comprises image-to-image translation or pix2pix translation with handmade labeling which precisely or exactly mimics shapes of curved and bent bands in a chromosome.

7. The method of claim 1, further comprising staining a metaphase chromosome to form a banding pattern on the chromosome comprising the cryptic deletion and photographing or scanning the banding pattern to produce the image of a chromosome prior to converting said image into an ideogram.

8. The method of claim 1, further comprising autoclassifying the chromosome comprising the cryptic deletion as normal, abnormal, or potentially abnormal.

9. The method of claim 1, further comprising generating or providing computer-generated text describing one or more chromosomal abnormalities or putative abnormalities comprising the cryptic deletion.

10. The method of claim 1, further comprising enhancing the chromosome image of the chromosome comprising the cryptic deletion without adding or deleting information prior to converting the image into an ideogram.

11. The method of claim 1, in which all chromosomes in a subject's karyotype are converted to ideograms.

12. The method of claim 1, further comprising converting the chromosome ideogram into an image of a real chromosome to confirm the chromosomal bands with respect to banding in a standard ISCN ideogram.

13. The method of claim 1, wherein the ideogram of the paired control chromosome is a normal human chromosome and/or wherein the ideogram of the paired control chromosome is of an abnormal human chromosome comprising the cryptic deletion.

14. The method of claim 1, wherein the ideogram of the paired control chromosome is described by the International System for Human Cytogenetic Nomenclature (ISCN-2005).

15. The method of claim 1, further comprising producing a karyotype of chromosomes in the sample comprising the cryptic deletion.

16. The method of claim 1, wherein said identifying employs the ideogram to further identify an exact break point of a chromosome, to further identify a chromosomal duplication, to further identify a chromosomal inversion, or to further identify a chromosomal translocation.

17. The method of claim 1, wherein the control ideogram of the paired control chromosome is obtained from a chromosome paired with the chromosome containing the cryptic deletion.

18. The method of claim 1, wherein obtaining an image of a banding pattern of a chromosome comprising a cryptic deletion comprises obtaining images from multiple chromosomes in a karyotype.

19. The method of claim 1, further comprising treating the subject for a disease, disorder, or condition associated with the chromosome identified as containing the cryptic deletion.

20. The method of claim 1, wherein the identifying a difference in a banding pattern of a chromosome comprises manual visual inspection of the ideogram containing a cryptic deletion or putative cryptic deletion and the paired control ideogram or evaluation of the ideogram and paired control ideogram using artificial intelligence.

* * * * *